United States Patent [19]
Soleta et al.

[11] Patent Number: 5,213,982
[45] Date of Patent: May 25, 1993

[54] HEATED DILUTION METHOD FOR A LIQUID SAMPLE

[75] Inventors: Donald D. Soleta, St. Louis, Mo.; Russell M. Morris, Deer Park, Tex.

[73] Assignee: Phillips Petroleum Company, Bartlesville, Okla.

[21] Appl. No.: 945,996

[22] Filed: Sep. 15, 1992

Related U.S. Application Data

[63] Continuation of Ser. No. 617,321, Nov. 23, 1990, abandoned.

[51] Int. Cl.$^5$ .................. G01N 1/00; G01N 31/00
[52] U.S. Cl. .................. 436/179; 436/180; 436/174; 436/163; 422/75; 422/81
[58] Field of Search .......... 436/179, 180, 174, 163, 436/161, 51; 73/863.11, 863.83; 422/68.1, 70, 75, 81, 100

[56] References Cited

U.S. PATENT DOCUMENTS

| | | | |
|---|---|---|---|
| 3,273,402 | 4/1964 | Farr | 436/180 |
| 3,961,054 | 6/1976 | Furia et al. | 514/187 X |
| 4,070,913 | 1/1978 | Roof | 73/422 |
| 4,148,610 | 4/1979 | Miller, Jr. et al. | 436/179 X |
| 4,271,703 | 6/1981 | Roof | 73/863.11 |
| 4,345,628 | 8/1982 | Campbell et al. | 436/179 |
| 4,633,413 | 12/1986 | Caueney et al. | 364/500 |
| 4,794,806 | 1/1989 | Nicoli et al. | 436/179 |

Primary Examiner—James C. Housel
Assistant Examiner—Long V. Le
Attorney, Agent, or Firm—George E. Bogatie

[57] ABSTRACT

An analyzer system for improving quality of a reaction product, wherein a liquid sample must be maintained at an elevated temperature to prevent precipitation of titratable species, comprises a heated sample and dilution section, an autotitrator and a programmable controller. In operation a liquid sample to be analyzed is withdrawn from a reactor and maintained at reactor temperature while being diluted. The diluted sample is then cooled and passed to an autotitrator for analysis. The analyzer system includes a programmable controller for automatic unattended dilution of successive samples.

7 Claims, 3 Drawing Sheets

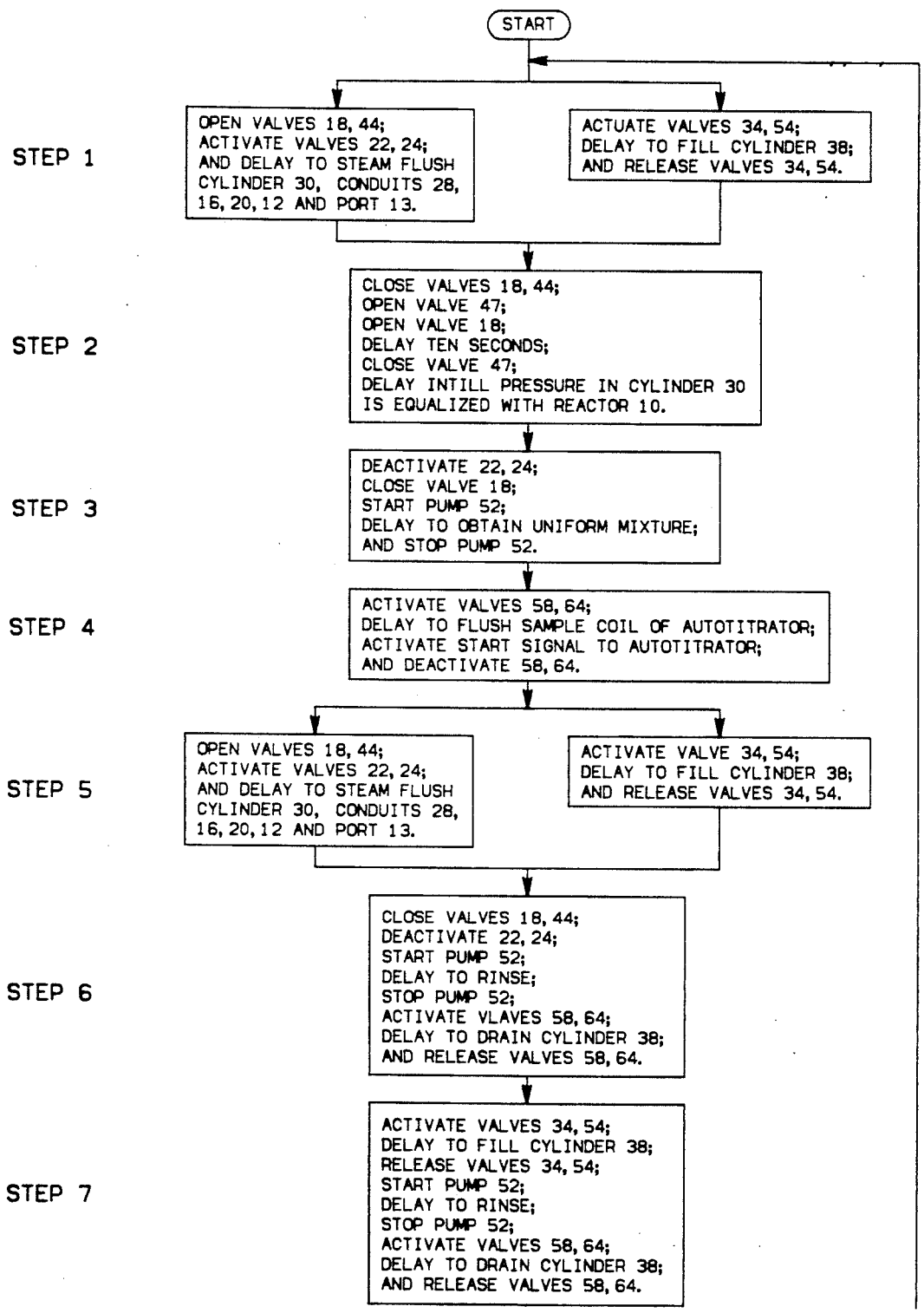

HEATED DILUTION METHOD FOR A LIQUID SAMPLE

This application is a continuation of application Ser. No. 617,321, filed Nov. 23, 1990 now abandoned.

This invention relates to chemical analysis of a diluted sample. In one aspect this invention relates to method and apparatus for obtaining and diluting samples of solutions which must be maintained at an elevated temperature to prevent precipitation of titratable species. In another aspect this invention relates to method and apparatus for analysis of a material by titration.

BACKGROUND OF INVENTION

As used herein, a pH titration involves the incremental addition of a standard acid to a carefully measured quantity of aqueous solution during which pH values and the aliquots of reagent added are recorded. A titration curve si a plot of these data. The titration curve is invaluable in determining the equivalence point in a pH titration. One problem encountered in the analysis of certain materials is that of preparing a diluted sample of the material, when the material to be analyzed must be dissolved at elevated temperatures. For example, titration analysis can be valuable in determining the mole percent ratio of titratable species in a process for preparing sodium sulfide solutions by reacting sodium hydroxide with sodium hydrosulfide, provided the reaction material can be dissolved in a solution for titration analysis.

Accordingly, it is an object of this invention to provide method and apparatus suitable for titration analysis of materials which dissolve only at elevated temperature.

Another object of this invention is to provide an apparatus and method for diluting a highly viscous and corrosive sample material.

Still another object of this invention is to provide an apparatus for sample handling with heating and cooling.

Yet another object of this invention is to provide an apparatus and method for automatic, unattended dilution of a highly viscous and corrosive sample material.

SUMMARY OF THE INVENTION

In accordance with the present invention an apparatus and a method are disclosed wherein a liquid sample of material to be analyzed is withdrawn from a reactor at reactor temperature and flows under reactor pressure through a sample conduit having a predetermined volume. From the sample conduit the liquid sample flows into a first cylinder which is sealed off from other external pressure, and which has a volume greater than the sample conduit. Since flow of sample material from the reactor is a result of reactor pressure and the liquid sample material is allowed to accumulate in the first cylinder, the flow stops when the pressure in the first cylinder substantially equals the reactor pressure. Pressure transferring the sample material in this manner assures that the sample conduit is full of material when flow from the reactor stops. The thus obtained measured quantity of sample material contained in the sample conduit is diluted by mixing with a liquid diluent contained in a second cylinder, with the second cylinder having a predetermined volume relationship with the sample conduit, so as to provide a diluted sample of material suitable for analysis by titration.

In a preferred embodiment, the sample conduit, the first and second cylinders and valve means for selectively establishing fluid communication between the reactor, sample conduit, first cylinder and second cylinder, are located in a heated enclosure which is maintained at a temperature substantially equal to the temperature of the sample material withdrawn from the reactor. After dilution int eh heated enclosure, the diluted sample is cooled in a heat exchanger and passed to an autotitrator for automatic titration analysis. Further in accordance with a preferred embodiment, the sample material is obtained and diluted under a programmed sequence of valve operations generated by a suitable programmable controller. In this latter preferred embodiment, automatic unattended dilution of successive samples is achieved by employing control valves which can be remotely operated by signals generated in the programmable controller.

Other objects and advantages of the invention will be apparent from the foregoing brief description of the invention and the appended claims as well as the detailed description of the drawings in which:

BRIEF DESCRIPTION OF THE DRAWINGS

FIG. 3 is a flow diagram for programming a programmable controller, which illustrates the sequence of valve operation for obtaining and diluting a sample of material.

DESCRIPTION OF THE PREFERRED EMBODIMENT

The invention is descried in terms of a particular configuration of an analyzer system and in terms of a particular sampling and diluting apparatus configuration. The invention is applicable, however, to any apparatus configuration which accomplishes the purpose of the invention. The invention is also described in terms of sampling a sodium sulfide reactor but is generally applicable to liquid samples which must be diluted at an elevated temperature.

Figure 1:
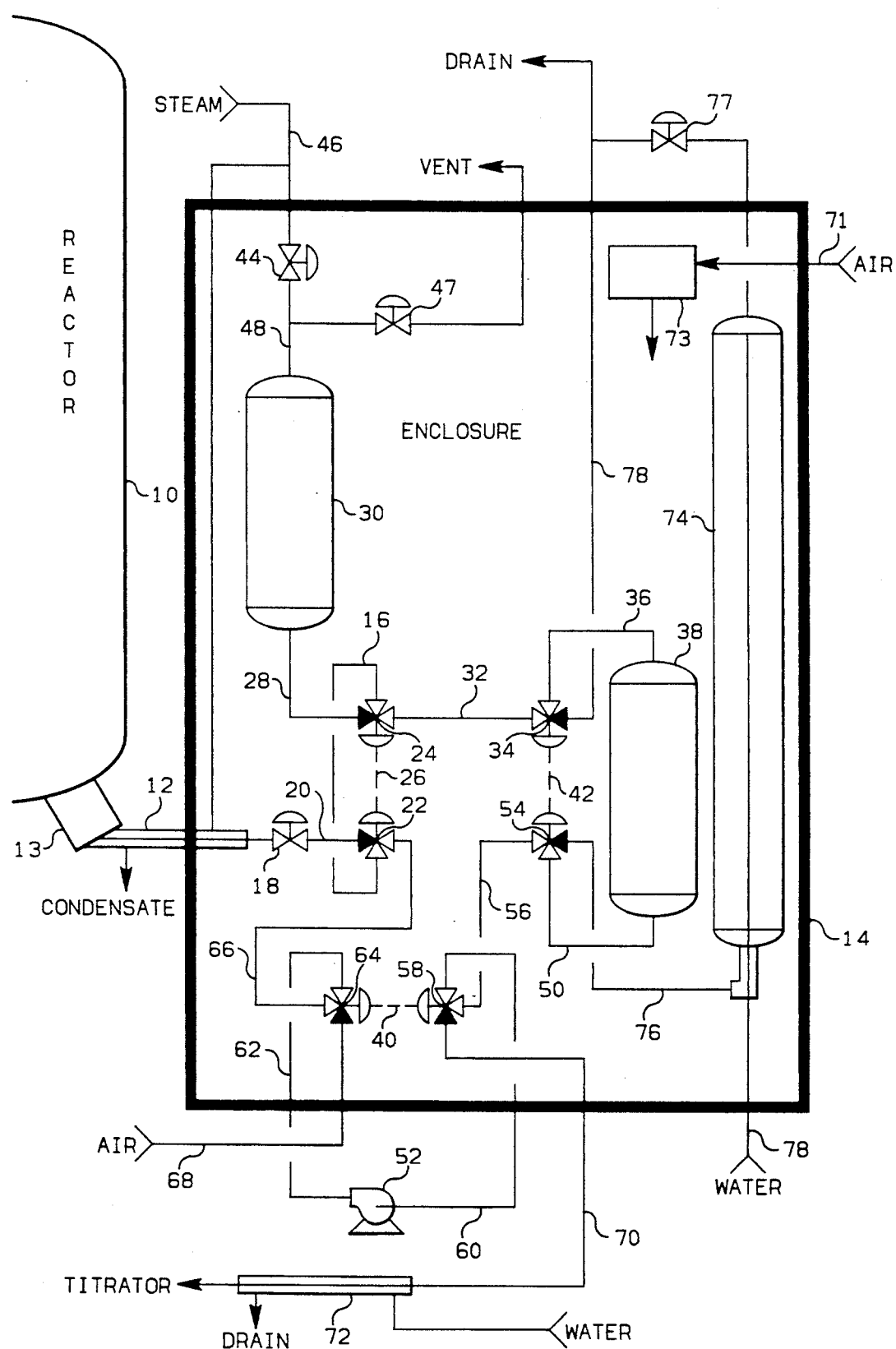
FIG. 1 is a diagrammatic representation of a liquid dilution system together with apparatus for obtaining a sample of a material according to the invention.

The pairs of 3-way diverting valves such as 22 and 24, as well as other pairs of 3-way valves illustrated in FIG. 1, are ganged together to operate simultaneously as indicated by the dashed lines 26, 40 and 42. Also on all of the 3-way valves illustrated in FIG. 1, the solid black port indicates the blocked port for diverting liquid in the valves, when the valve is in tis normal or unactivated state. In the active state of the 3-way valves illustrated in FIG. 1, the port opposite the solid black pot is blocked.

Referring now to FIG. 1, a sample of liquid reaction product is withdrawn from reactor 10 under reaction conditions. A point is selected on the reactor for installing a sample take-off port 13 to obtain a representative sample of reaction product, and the liquid sample is forced by reactor pressure to flow from reactor 10 through steam heated conduit 12 into the heated enclosure 14. In the enclosure 14 the sample material flows through an arrangement of valves and conduits, as will be more fully described hereinafter, the accumulates in holding cylinder 30 which is sealed off from other externally applied pressure. Cylinder 30 is preferably teflon lined for holding corrosive material.

Flow of sample material form the reactor 10 to the closed cylinder 30 continues until the pressure in cylinder 30 substantially equalizes with the pressure in reactor 10. Since the sample material flows through the sample conduit 16 prior to entering the cylinder 30, there is assurance that the sample conduit 16 is completely full of sample material when flow from the reactor stops.

The liquid stream flowing in conduit 12 is provided to one end of the sample conduit 16 via block valve 18, conduit 20, and 3-way valve 22. The sample conduit 16, which extends between 3-way valves 22 and 24, has a predetermined volume, for example, a volume of about 18 mL. the volume of about 18 mL for the sample conduit is suitable for sampling reaction material from a sodium sulfide reactor for analysis by an autotitrator. From the sample conduit 16 the sample liquid flows through 3-way valve 24 and conduit 28, into a holding cylinder 30 when a liquid sample is being withdrawn from the reactor 10. When the liquid sample s being diluted, however, the liquid flowing from sample conduit 16 is diverted by 3-way valve 24 to flow through the combination of conduit 32, 3-way valve 34 and conduit 36 into mixing cylinder 38. For diluting an 18 mL sample of sodium sulfide solution, the volume of cylinders 38 can be about 1 liter.

From the cylinder 30 sample liquid may be returned to the reactor 10 via the sample loop 16 and the combination of valves 18, 22 and 24 under steam pressure, which is supplied form an external source via valve 44 and the combination of conduits 46 and 48. The external steam source also supplies heat to conduit 12 via conduit 46.

From cylinder 38, which initially contains a predetermined volume of a suitable liquid diluent, liquid may be withdrawn for diluting the sample material in sample conduit 16. The diluent liquid is directed to flow in a closed loop pathway which includes sample conduit 16. The closed pathway is via conduit 50, 56, 60, 62, 66, 16, 32 and 36, which includes 3-way valves 54, 58, 64, 22, 24 and 34, and also pump 52. Circulation of the measured quantity of sample material from sample conduit 16 and the measured quantity of liquid diluent from cylinder 38 is continued until a substantially uniform mixture thereof is obtained. Any suitable length of mixing time and flow rate in the closed loop pathway may be utilized. The exact time required for each specific apparatus configuration being dependent upon the relative volume of the closed loop pathway, the speed and capacity of the pump 52, the solubility and mobility of the sample material in the diluent liquid, the turbulence of flow through the closed loop pathway and other similar parameters. For a sample material of 18 mL of sodium sulfide solution which is combined with 1 liter of hot distilled water in cylinder 38, a flow rate in the closed pathway of about 1 liter per minute for a time period of about 5 minutes has been found to be satisfactory.

Air pressure supplied via conduit 68 may be used to force the uniformly diluted sample material form the enclosure 14 through conduit 70. The uniformly diluted sample, which is representative of the reaction material, is cooled in heat exchanger 72 and transported to an analyzer instrument such as a titrator, or for other use of the diluted sample material, via conduit 70.

Cylinder 38 can be refilled with diluent from supply cylinder 74 via conduits 76 and 50, and valve 54. To insure complete filling of cylinder 38, it may be filled to overflow so as to cause a flow to drain via valve 34 and conduit 78. Cylinder 74, which is preferably about 3 times as large as cylinder 38, is maintained full of diluent liquid to provide a preheated supply of diluent liquid. The diluent liquid may be supplied under pressure to cylinder 74 from an external source via conduit 78 to maintain cylinder 74 full of liquid.

The enclosure 14 will preferably be maintained at a temperature substantially equal to the temperature o the reaction material in reactor 10. The temperature of the reaction material will typically be 260° F. or greater. The invention is applicable, however, to higher or lower temperatures, depending on the temperature required to maintain the sample material in a soluble state for dilution and analysis by titration after dilution.

Temperature control of the enclosure 14 is accomplished by means of the air heater 73. Air is supplied to the air heater 73 via conduit 71 and the heater 73 is controlled in a conventional manner to maintain a desired temperature in enclosure 14.

Figure 2:
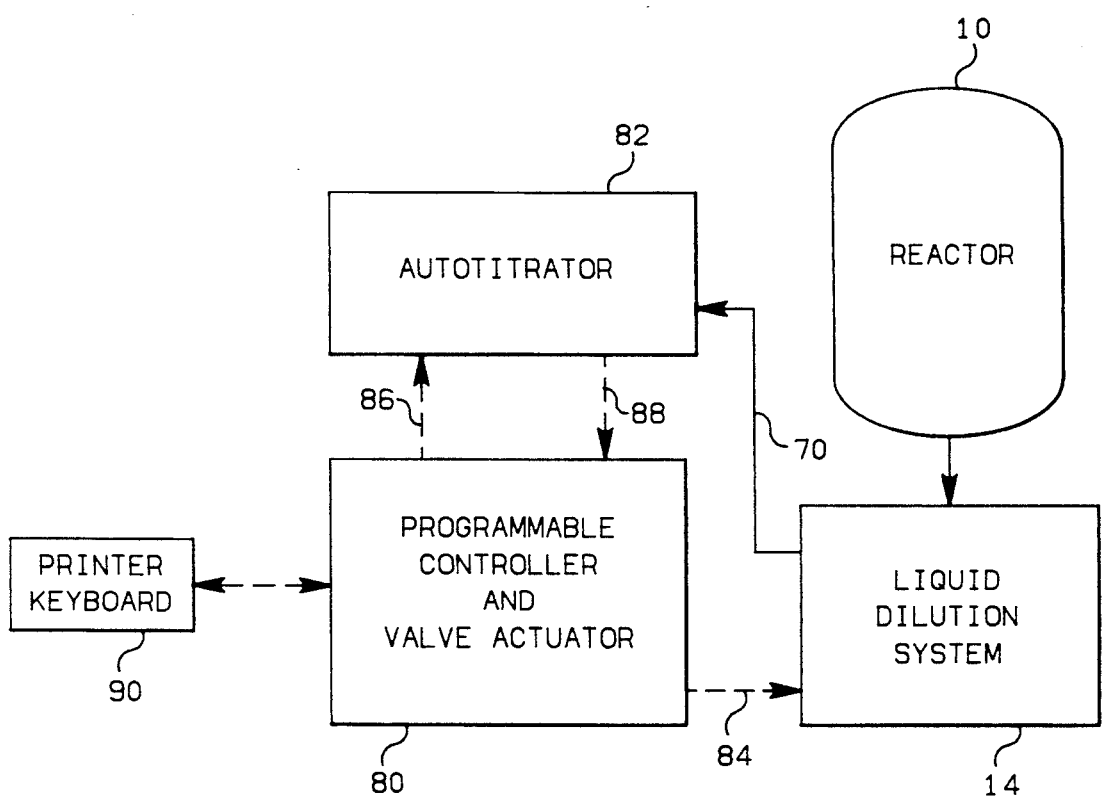
FIG. 2 is a block diagram of an analyzer system incorporating the liquid dilution system illustrated in FIG. 1.

Referring now to FIG. 2, where like reference numerals are used for the parts which are also illustrated in FIG. 1, there is illustrated a block diagram of an analyzer system for analyzing a diluted sample obtained from the reactor 10. The analyzer system includes the heated dilution system in enclosure 14, a programmable controller (PC) 80 having a valve actuator section and printer/keyboard 90, and an autotitrator 82. This analyzer system enhances reactor product quality by insuring more uniform reaction products. Any suitable autotitrator may be utilized in the practice of this invention, an example of an autotitrator is an IONICS 3000 AUTOTITRATOR.

The PC 80 orchestrates operation of the sample dilution 14 and the autotitrator 82 by providing suitable signals via lines 84 and 86 respectively. The signal line 84 represents a plurality of signals which are provided so as to properly sequence the valves illustrated in FIG. 1. The valve actuator section of the PC 80 is a preferred means for supplying pneumatic pressure signals to pneumatic actuators, which can be associated with valves 18, 22, 24, 34, 44, 47, 54, 58 and 64 illustrated in FIG. 1 for remotely operating these valves. The invention, however, is also applicable to electrical, mechanical, hydraulic or other signal transmitting means. The PC 80 also provides a start analysis signal 86 to the autotitrator 82 and receives an autotitrator ready signal 88 from the autotitrator 82. Any suitable PC having the capability of remotely operating control valves in a programmed sequence can be used in the practice of this invention. Suitable programmable controllers and control valves are described at length in chapter 6.4 of Liptak, B. G. "Instrument Engineer Handbook" Process Control, Chilton Book Co., 1985.

Referring now to FIG. 3, the sequence requirement for opening and closing valves 18, 22, 24, 34, 4, 47, 54, 58 and 64, which are shown in FIG. 1, is illustrated by a flow diagram. In the flow diagram all 2-way valves are assumed to be initially closed and all 3-way valves are initially in their normal (unactuated) position as shown in FIG. 1.

The first step in the sample dilution sequence flushes the cylinder 30 and the sample conduit 16 with steam, with the steam and any other material flushed from the cylinder or conduit being passed into the reactor 10. This step returns any residual sample material in cylinder 30 or sample conduit 16 back into the reactor 10.

The delay associated with this step, and with other delays associated with all of the subsequent steps, will depend upon a number of factors such as the volume of the cylinders, the steam pressure utilized, the solubility and mobility of the sample material being analyzed, the valve and conduit sizes utilized, and other similar parameters. The time required for any of these steps in a particular operation will generally be obvious to a person skilled in the art. For example, in a prototype operation according to this invention, which utilized ¼" conduits for handling sodium sulfide solution, 1 liter cylinders, 40 psig steam, etc., a flush time of 2 minutes was found to be satisfactory.

Step 2 begins withdrawal of the sample material from the reactor 10 while cylinder 30 is being vented through valve 47 for ten seconds after sample material withdrawal begins. Sample withdrawal continues until the pressure in cylinder 30 equalizes with the pressure in reactor 10. During this time cylinder 30 is at least partially filled with sample material and sample conduit 16 is completely filled with sample material while cylinder 38 is completely refilled with diluent liquid.

Step 3 prevents flow of sample material form the reactor 10 at a time that insures the sample conduit 16 is filled with sample material, and further isolates the sample conduit 16 from the cylinder 30 while connecting the sample conduit and cylinder 38 in a closed loop via valves 54, 58, 64, 22, 24 and 34. Step 3 also causes mixing of the measured quantity of sample material in sample conduit 16 with the measured quantity of diluent liquid in cylinder 38 for a time period necessary to obtain a uniform mixture.

Step 4 transports the diluted sample material to the autotitrator 82, and the PC 80 issues a start signal to the autotitrator.

Step 5 flushes the cylinder 30 and the sample conduit 16 with steam into reactor 10 and fills cylinder 38 with diluent liquid.

Step 6 circulates the diluent liquid contained in cylinder 38 through a closed path, which includes sample conduit 16 and the cylinder 38, so as to wash these components. For the above mentioned prototype system, using distilled water as the diluent liquid, a wash period of four minutes was utilized. Step 6 concludes by draining this wash liquid via conduit 70 through a drain in the autotitrator 82.

Step 7 repeats the wash cycle by first filling cylinder 38 with diluent liquid and then circulating the liquid through a closed path, which includes sample conduit 16 and the cylinder 38. The wash liquid is drained via conduit 70 as in Step 6.

Step 8 requires the PC 80 to wait before starting the next sampling-analysis sequence. On completion of the analysis, the autotitrator 82 returns a ready signal to the PC and the sampling-analysis sequence starts again at Step 1.

The following example illustrates analysis of sample material withdrawn from a sodium sulfide reactor wherein the sample contains a minor amount of sodium hydrosulfide. This example is intended to further assist one skilled in the art to an understanding of this invention and is not limitable of the reasonable scope of this invention.

EXAMPLE I

This example shows that the inventive sampling, dilution and titration technique, which was carried out in conjunction with a pilot plant reactor, gave values for titratable species which corresponded favorably in magnitude to the values for these species calculated for combined portions of more concentrated stock solutions. For purposes of this example, commercially available solutions containing a major amount of sodium sulfide ($Na_2S$) and a minor amount of sodium hydrosulfide (NaSH) were prepared by mixing the necessary quantities of a commercially available sodium hydroxide solution (NaOH) and a commercially available sodium hydrosulfide solution (NaSH). The minor amount of sodium hydrosulfide (NaSH) desired in the system was about 3 mole % based on the total amount of $Na_2S$ in the mixture.

The following equation (i) describes the reaction which takes place on mixing the commercially available solutions of NaOH and NaSH:

$$NaOH + NaSH \rightarrow Na_2S + H_2O \qquad (i)$$

According to the stoichiometry, one mole of NaOH reacts with one mole of NaSH to give one mole of $Na_2S$ and one mole of $H_2O$. Since it was desired to prepare concentrated solutions of $Na_2S$ containing about 3 mole % of NaSH based on total $Na_2S$, the amount of NaSH added was appropriately adjusted to the desired stoichiometric excess over NaOH. Table I summarizes the amounts used in designated samples, I, II, III and IV.

TABLE I

Concentrated Stock Solutions of $Na_2S$ Prepared From Commercially Available Solutions of $NaOH^a$ and $NaSH^b$

| Reference | lb Commercial NaOH Solution | lb Commercial NaSH Solution | Approximate Molar % Excess $NaSH^c$ |
|---|---|---|---|
| Sample I | 76.0 | 88.3[e] | 3.5 |
| Sample II | 76.1 | 88.2[f] | 3.2 |
| Sample III | 76.0 | 88.2 | 3.3 |
| Sample IV | 76.1 | 88.3 | 3.3 |

[a]The commercial aqueous sodium hydroxide solution was about 47.1 weight percent NaOH.
[b]The commercial aqueous sodium hydrosulfide solution was about 58.8 weight percent NaSH and contained about 0.3 weight percent sodium sulfide ($Na_2S$).
[c]Takes into account the 0.003 lb mole $Na_2S$ added in the NaSH solution.
[d]The 76.0 lb portions of NaOH solution contained 0.895 lb mole of NaOH and the 76.1 lb portions contained 0.896 lb mole of NaOH.
[e,f]The 88.2 and 88.3 lb portions of the NaSH solution contained, respectively, 0.925 and 0.926 lb mole of NaSH.

From the facts given in Table I, it is apparent that the original mixtures which were diluted, sampled and titrated in accordance with the inventive procedure contained titratable species $Na_2S$ and NaSH.

The following equations (ii) and (iii) describe the step-wise reactions which occur in the HCl titration of the diluted $Na_2S$ solution:

$$Na_2S + HCl \rightarrow NaSH + NaCl \qquad (ii)$$

$$NaSH + HCl \rightarrow H_2S + NaCl \qquad (iii)$$

The "first endpoint" corresponds to that point at which sufficient HCl has been added to convert all the $Na_2S$ to NaSH and NaCl. The "second endpoint" corresponds to that point at which sufficient HCl has been added to convert all the NaSH to $H_2S$ and NaCl. According to the stoichiometry, the amount of HCl theoretically required to reach the "first endpoint" would be the same as that required to reach the "second endpoint" if $Na_2S$ were the only titratable specie in the original mixture.

Equation (ii), e.g., indicates that one mole of $Na_2S$ reacts with one mole of HCl to give one mole of NaSH and one mole of NaCl. Equation (iii), e.g., indicates that one mole of NaSH reacts with one mole of HCl to give one mole of H$_2$S and one mole of NaCl.

In the instant operation, the desired stock solution was prepared to have about a 3 molar % concentration of NaSH in the original Na$_2$S solution based on the concentration of sodium sulfide (see Table I). Titration of these systems, designated as samples I, II III and IV, would thus require more HCl to reach the "second endpoint" than was required to reach the "first endpoint". This follows from the fact that the second phase of the titration involves the reaction of the NaSH produced in equation (ii) with HCl as well as reaction of the additional NaSH reagent deliberately added to the original Na$_2$S solution preparation. This difference in the amounts of HCl required, respectively, to reach the "first endpoint" and "second endpoint" corresponds to the excess of NaSH provided in the preparation of the original Na$_2$S solutions.

Titrations of the samples I, II, III and IV summarized in Table II were carried out to determine the molar % excess of NaSH in each of the systems.

TABLE II

Titrations of Na$_2$S Solutions Prepared from Commercially Available NaOH[a] and NaSH[b] Solutions

| Sample | Column 1 mmoles HCl to EP-1[c] | Column 2 mmoles HCl to EP-2[d] | Column 3 Excess mmoles HCl[e] (EP-2) − (EP-1) | Column 4 % Molar Excess NaSH (Titration)[g] | Column 5 % Molar Excess NaSH (Table I) |
|---|---|---|---|---|---|
| I | 0.449 | 0.465 | 0.016 | 3.6 | 3.5 |
| II | 0.469 | 0.482 | 0.013 | 2.8 | 3.2 |
| III[f] | 0.531 | 0.546 | 0.015 | 2.8 | 3.3 |
| IV | 0.464 | 0.478 | 0.014 | 3.0 | 3.3 |

[a] See footnote a in Table I.
[b] See footnote b in Table I.
[c] EP-1 represents first endpoint: the mmoles HCl values cited in I, II and IV are the averages of 3 titration runs.
[d] EP-2 represents second endpoint: the mmoles HCl values cited in I, II and IV are the averages of 3 titration runs.
[e] Values also correspond numerically to excess mmoles of NaSH in the system.
[f] The mmoles HCl values are the averages of 5 titration runs.
[g] The values in column 4 were calculated by dividing the values in column 3 by the values in column 1 and multiplying the quotient by 100.

Referring to the results in Table II, it can be seen that the molar % excess value for NaSH determined by the inventive sampling, dilution and titration technique agreed favorably with the analogous values based on the weighed quantities of commercial solutions of NaOH and NaSH which were mixed to give the original unreacted Na$_2$S/NaSH solutions.

That which is claimed is:

1. A method of obtaining a sample of a reaction solution containing a material which dissolves only at an elevated temperature and diluting said sample for chemical titrametric analysis, said method comprising:
   a) venting a first vessel to atmospheric pressure;
   b) after step a), establishing flow of said reaction solution to be analyzed from an elevated pressure in a reactor and directing low of said reaction solution through a sample conduit having a pre-determined volume, and then into said first vessel while maintaining said reaction solution at said elevated temperature;
   c) after step b), sealing off said first vessel from atmospheric pressure;
   d) allowing flow of said reaction solution to accumulate in said first vessel until the pressure in said first vessel substantially equals the pressure in said reactor, thereby assuring that said sample conduit is full of said reaction solution when flow stops, wherein the volume of reaction solution in said sample conduit provides said sample of reaction solution;
   e) diluting said sample of reaction solution at said elevated temperature by mixing with a predetermined volume of liquid diluent contained in a second vessel to provide a diluted sample;
   f) passing said diluted sample to a titrametric analyzer; and
   g) backflushing reaction solution in said first vessel and said sample conduit to said reactor.

2. A method in accordance with claim 1, wherein said sample conduit is connected between corresponding first ports on each of a first pair of three-way valves and said first vessel is connected to a second port on one of said first pair of three-way valves, said first pair of three-way valves having first and second positions, wherein said reactor includes a sample take-off port, and wherein said step for directing flow of reaction solution comprises:
   flowing said reaction solution from said sample take-off port through a heated conduit having a block valve located therein and then to the second port on the other one of said first pair of three-way valves; and
   placing said first pair of three-way valves in said second position, whereby fluid communication is established between said reactor and said first vessel.

3. A method in accordance with claim 2, wherein said second vessel is connected between corresponding first ports on a second pair of three-way valves and a pump is connected between corresponding first ports on a third pair of three-way valves, said second and third pair of three-way valves having first and second positions, wherein said step of diluting said sample comprises:
   placing each of said first, second and third paris of three-way valves in aid first position so as to interconnect said sample conduit, said second vessel and said pump to form a closed loop pathway; and
   operating said pump so as to mix said sample and said diluent liquid by circulating said sample and said diluent liquid in said closed loop pathway.

4. A method in accordance with claim 3, wherein said reaction solution flowing from said reactor is maintained at said elevated temperature by heating an enclosure containing said first and second vessels, said sample conduit and said first, second and third pairs of three-way valves.

5. A method in accordance with claim 4 wherein a vent conduit having a first two-way valve operably located therein, and a steam supply conduit having a second two-way valve operably located therein, are connected to said first vessel, said method additionally comprising:

connecting a programmable controller for operating said first, second and third pair of three-way valves, said first and second two-way valve, said block valve and said pump, said programmable controller being programmed to automatically operate said valves and pump in the following sequence:

a) close said first two-way valve and open said second two-way valve to admit steam into said first vessel;

b) place said first pair of three-way valves in said second position and open said block valve so as to backflush a flushed solution from said first vessel and said sample conduit into said reactor;

c) hold the position of said block valve, first and second two-way valves and first pair of three-way valves set froth in paragraphs of a) and b) for a length of time sufficient to flush any reaction solution in said first cylinder and said sample conduit into said reactor;

d) close said second two-way valve and said block valve and open said first two-way valve to vent said first vessel to atmosphere;

e) open said block valve and then delay for about 10 seconds and close said first two-way valve;

f) wait until the pressure in said first vessel is substantially equal to the pressure in said reactor;

g) after step f), close said block valve and place said first, second and third pair of three-way valves in said first position; and h) operate said pump to mix said sample and diluent fluid.

6. A method in accordance with claim 4, wherein said reactor solution comprises sodium sulfide as a major component and sodium hydrosulfide as a minor component.

7. A method for determining excess of a minor component in a sample comprising a sodium sulfide reaction solution containing a minor component of sodium hydrosulfide which dissolves only at an elevated temperature, wherein the determination is based on two end point pH titrations, said method comprising the following steps:

a) venting a first vessel to atmospheric pressure;

b) after step a), establishing flow of said reaction solution to be analyzed from an elevated pressure in a reactor and directing flow of said reaction solution through a sample conduit having a predetermined volume, and then into said first vessel while maintaining said reaction solution at said elevated temperature;

c) after step b), sealing off said first vessel from atmospheric pressure;

d) allowing flow of said reaction solution to accumulate in said first vessel until the pressure in said first vessel substantially equals the pressure in said reactor, thereby assuring that said sample conduit is full of said reaction solution when flow stops, wherein the volume of reaction solution in said sample conduit provides said sample of reaction solution;

e) diluting said sample of said reaction solution at said elevated temperature by mixing with a predetermined volume of liquid diluent contained in a second vessel to provide a diluted sample;

f) cooling said diluted sample to about ambient temperature;

g) titrating said diluted sample to obtain said two end point pH titration of sodium sulfide and sodium hydrosulfide, wherein a greater quantity of acid reagent added for extinction of sodium hydrosulfide than for sodium sulfide indicates excess of sodium hydrosulfide; and h) backflushing said reaction solution in said first vessel and said sample conduit to said reactor.

* * * * *

UNITED STATES PATENT AND TRADEMARK OFFICE
CERTIFICATE OF CORRECTION

PATENT NO. : 5,213,982
DATED : May 25, 1993
INVENTOR(S) : Donald D. Soleta, et al.

It is certified that error appears in the above-identified patent and that said Letters Patent is hereby corrected as shown below:

In the drawings, FIG. 3, the lower part of the diagram has been deleted. Attached is a copy of the complete FIG. 3 for substitution in the above-identified patent.

Signed and Sealed this

First Day of March, 1994

Attest:

BRUCE LEHMAN

Attesting Officer

Commissioner of Patents and Trademarks